United States Patent
Strohmaier et al.

(10) Patent No.: US 6,559,324 B2
(45) Date of Patent: *May 6, 2003

(54) METHOD FOR MANUFACTURING CALCIUM SALTS OF HIGHLY UNSATURATED FATTY ACIDS

(75) Inventors: George K. Strohmaier, Medina, OH (US); Eiler D. Fredericksen, Henderson, NV (US)

(73) Assignee: Norel Acquisition Corp., Fairlawn, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/109,379

(22) Filed: Mar. 28, 2002

(65) Prior Publication Data

US 2002/0137958 A1 Sep. 26, 2002

Related U.S. Application Data

(63) Continuation of application No. 09/675,745, filed on Sep. 29, 2000, now Pat. No. 6,392,075.

(51) Int. Cl.$^7$ ............................................. C07C 51/00
(52) U.S. Cl. ........................................ 554/156; 426/807
(58) Field of Search ........................... 889/156; 426/807

(56) References Cited

U.S. PATENT DOCUMENTS

| 4,642,317 A | 2/1987 | Palmquist et al. | 514/558 |
|---|---|---|---|
| 4,826,694 A | 5/1989 | McAskie | 426/74 |
| 5,004,728 A | 4/1991 | Chalupa et al. | 514/12 |
| 5,143,737 A | 9/1992 | Richardson | 426/2 |
| 5,250,307 A | * 10/1993 | Cummings et al. | 426/72 |
| 5,416,115 A | 5/1995 | Erdman et al. | 514/560 |
| 6,392,075 B1 | * 5/2002 | Strohmaier et al. | 554/156 |

* cited by examiner

*Primary Examiner*—Deborah D. Carr
(74) *Attorney, Agent, or Firm*—Synnestvedt & Lechner LLP

(57) ABSTRACT

A method for the preparation of free-flowing calcium salts of highly unsaturated fatty acids, which includes the steps of:
  (a) providing a fatty acid feedstock consisting essentially of:
    (i) from about 50 to about 95% by weight of unsaturated C:16-C:22 fatty acids;
    (ii) from about 5 to about 40% by weight of saturated C:14-C:22 fatty acids; and
    (iii) no more than about 6% by weight of moisture, insolubles and unsaponifiables,
  with no more than about 20% by weight of the unsaturated feedstock being in the form of glycerides;
  (b) adding to the unsaturated feedstock from about 1.0 to about 2.5 equivalents of calcium oxide relative to the unsaturated feedstock, so that a reactive admixture is formed; and
  (c) adding to the reactive admixture from about 2 to about 5 equivalents of water relative to the calcium oxide, so that the calcium oxide hydrates and neutralizes the fatty acids to form the calcium salts;
provided that when less than 1.75 equivalents of calcium oxide is added, the unsaturated feedstock comprises at least 25% by weight of the saturated fatty acids and is heated to a temperature above its melting point before the step of adding the calcium oxide.

13 Claims, No Drawings

METHOD FOR MANUFACTURING CALCIUM SALTS OF HIGHLY UNSATURATED FATTY ACIDS

CROSS REFERENCE TO RELATED APPLICATION

This application is a Continuation of U.S. patent application Ser. No. 09/675,745 filed Sep. 29, 2000, now U.S. Pat. No. 6,392,075 the disclosure of which is incorporated herein by reference.

BACKGROUND OF THE INVENTION

The present invention relates to a process for the production of rumen bypass feed supplements that are useful as an energy source for ruminants. The process converts highly unsaturated fatty acids to their respective calcium salts. In particular, the present invention relates to a process for the production of calcium salts of unsaturated fatty acids that are of particular interest as nutritional supplements, such as conjugated linoleic acids (CLA's). The calcium salts of the present invention, when fed to cattle, result in the production of milk and meat that is enriched with the unsaturated fatty acid of interest.

CLA's have become the focus of numerous research programs that seek to capitalize on their nutritional, therapeutic and pharmacologic properties. In 1978, researchers at the University of Wisconsin discovered the identity of a substance in cooked beef that appeared to inhibit mutagenesis. This substance was found to be a CLA.

The biological activity associated with CLA's is diverse and complex. Anticarcinogenic properties have been well documented, as well as stimulation of the immune system. U.S. Pat. No. 5,914,346 discloses the use of CLA's to enhance natural killer lymphocyte function. U.S. Pat. No. 5,430,066 describes the effect of CLA's in preventing weight loss and anorexia by immune system stimulation.

CLA's have also been found to exert a profound generalized effect on body composition, in particular, upon redirecting the partitioning of fat and lean tissue mass. U.S. Pat. Nos. 5,554,646 and 6,020,378 disclose the use of CLA's for reducing body fat and increasing lean body mass. U.S. Pat. No. 5,814,663 discloses the use of CLA's to maintain an existing level of body fat or body weight in humans. U.S. Pat. No. 6,034,132 discloses the use of CLA's to reduce body weight and treat obesity in humans. CLA's are also disclosed by U.S. Pat. No. 5,804,210 to maintain or enhance bone mineral content.

The beneficial effects produced by unsaturated fatty acids are not limited to CLA's. Other unsaturated fatty acids are disclosed to be useful for treating diabetes (U.S. Pat. No. 4,472,432), heart disease (U.S. Pat. Nos. 4,495,201; 5,541,225 and 5,859,055), prostaglandin deficiencies (U.S. Pat. No. 5,043,328), malaria (U.S. Pat. No. 5,604,258), osteoporosis (U.S. Pat. Nos. 5,618,558 and 5,888,541), cancer (U.S. Pat. No. 5,763,484), immune system function (U.S. Pat. No. 5,767,156), Huntington's Chorea (U.S. Pat. No. 5,837,731) and inflammation (U.S. Pat. No. 5,861,433).

The use of CLA-enriched foods to increase dietary levels of CLA is disclosed by U.S. No. 5,416,115. U.S. Pat. No. 5,143,737 discloses that the unsaturated fat content of milk and meat from ruminant animals can be increased by incorporating the intended unsaturated fat into the diet of the ruminant. Thus, meat and milk enriched with CLA's and other unsaturated fatty acids can be obtained by supplementing ruminant diets with unsaturated fatty acids such as CLA.

Unsaturated fatty acids, however, undergo hydrogenation to saturated fatty acids by microbial action in the rumen and must be fed to ruminants in a protected form. The aforementioned U.S. Pat. No. 5,143,737 discloses the encapsulation of unsaturated fatty acids with non-toxic organic materials to protect the unsaturated fatty acids from microbial action in the rumen. The most familiar form in which fatty acids in general are protected from microbial action in the rumen are the fatty acid calcium salts disclosed by U.S. Pat. Nos. 4,642,317; 4,826,694; 4,853,233 and 4,909,138. This form of fatty acid protection is widely accepted in the dairy and beef cattle industries.

Unsaturated fatty acids, however, do not readily react to form calcium salts using the processes disclosed by the above-listed patents. Instead of forming free-flowing granules, a mass develops that hardens into a tough material that resists grinding into the fine particles required for consumption by cattle. The resulting material also lacks storage stability. The product tends to auto-oxidize through an exothermic reaction that leads to a congealing of the product mass horn its free flowing granular state to a hard amorphous state, suggesting that significant quantities of unreacted starting materials are present in the final product.

To be commercially viable, rumen-protected unsaturated fatty acid cattle feed supplements must be in a form acceptable to the cattle industry. Therefore, a need exists for a process by which unsaturated fatty acids can be converted to calcium salts that are storage stable and easily formed into particles small enough for cattle to consume.

SUMMARY OF THE INVENTION

This need is met by the present invention. It has now been discovered that storage stable calcium salts of unsaturated fatty acids can be produced in fine particle form either by using elevated levels of calcium oxide, or by reducing the amount of unsaturated fatty acids in the fatty acid feedstock.

Therefore, according to one aspect of the present invention, a method is provided for the preparation of free-flowing calcium salts of highly unsaturated fatty acids, which includes the steps of (a) providing a fatty acid feedstock consisting essentially of
  (i) from about 50 to about 95% by weight of unsaturated C: I 6-C:22 fatty acids;
  (ii) from about 5 to about 40% by weight of saturated C:14-C:22 fatty acids; and
  (iii) no more than about 6% by weight of moisture, insolubles and unsaponifiables,
with no more than about 20% by weight of the unsaturated feedstock being in the form of glycerides;

(b) adding to the unsaturated feedstock from about 1.0 to about 2.5 equivalents of calcium oxide relative to the unsaturated feedstock, so that a reactive admixture is formed; and (c) adding to the reactive admixture from about two to about five equivalents of water relative to the calcium oxide, so that the calcium oxide hydrates and neutralizes the fatty acids to form the calcium salts;

provided that when less than 1.75 equivalents of calcium oxide is added, the unsaturated feedstock comprises at least 25% by weight of the saturated fatty acids and is heated to a temperature above its melting point before the step of adding the calcium oxide.

Thus, one embodiment of this aspect of the present invention employs 1.75 equivalents of calcium oxide or greater to produce an unsaturated fatty acid calcium salt that readily forms a fine, granular free-flowing product that is considered acceptable by the cattle industry. This embodiment of the invention can be used with all levels of unsaturation in feedstocks and even with feedstocks that consist entirely of unsaturated fatty acids. In another embodiment of this aspect of the present invention, when lower amounts of calcium oxide are employed, the level of unsaturated fatty acids in the fatty acid feedstock must also be lowered by blending the feedstock with a second fatty acid feedstock having a lower level of unsaturated fatty acid.

For example, in a preferred embodiment of this aspect of the invention, an unsaturated fatty acid feedstock is employed containing from about 60 to about 70% by weight of CLA's, with the total level of unsaturated fatty acids ranging as high as 95% by weight. A fatty acid calcium salt suitable for use as a rumen bypass feed supplement can be produced by reacting this unsaturated fatty acid feedstock with 1.75 equivalents or greater of calcium oxide. To produce an acceptable fatty acid calcium salt with less calcium oxide, the CLA-containing feedstock must be blended with a second fatty acid feedstocks containing reduced levels of unsaturated fatty acids. For example, the CLA-containing feedstock can be blended with an amount of palm fatty acid distillate (PFAD) effective to increase the level of saturated fatty acids in the blend to at least 25% by weight. Other suitable sources of saturated fatty acids include tallow, lard, etc., or distilled or fractionated sources of individual saturated fatty acids.

Thus, the process of the present invention obtains free-flowing fatty acid calcium salt granules essentially free of unreacted unsaturated fatty acid starting material from fatty acid feedstocks containing levels of unsaturated fatty acids for which this was heretofore not possible.

Therefore, according to another aspect of the present invention, a free flowing highly unsaturated fatty acid calcium salt that is stable against oxidation is provided, prepared by the method of the present invention.

More specifically, the present invention incorporates the discovery that free-flowing calcium salts of unsaturated fatty acid feedstocks may be obtained by using an appropriate stoichiometric excess of calcium oxide and adjusting the amount of unsaturated fatty acids in the feedstock based upon the degree of calcium oxide in stoichiometric excess. While not being bound by any particular theory, it is believed that the heat of hydration of the calcium oxide promotes that neutralization reaction that forms the calcium salt and that the presence of saturated fatty acids plays an important role in promoting the calcium salt formation as well. The excess calcium hydroxide produced by calcium oxide hydration is also believed to function as a diluent in the finished product that promotes the ability of the finished product to be broken into fine particles.

Therefore, according to another aspect of the present invention, a free-flowing unsaturated fatty acid calcium salt product is provided having from 0.1 to about 1.5 equivalents of calcium hydroxide relative to the fatty acid content of the product, wherein the product has a fatty acid profile consisting essentially of:

(a) from about 50 to about 95% by weight of unsaturated C:16-C:22 fatty acids;

(b) from about 5 to about 40% by weight of saturated C: 14-C:22 fatty acids; and (c) no more than about 6% by weight of moisture, insolubles and unsaponifiables, and with no more than about 20% by weight of the fatty acid profile being in the form of glycerides;

provided that when less than 0.75 equivalents of calcium hydroxide is present the fatty acid profile contains at least 25% by weight of saturated fatty acid.

The above and other features and advantages of the present invention will become clear from the following description of the preferred embodiment.

DETAILED DESCRIPTION OF THE PREFERRED EMBODIMENTS

The present invention provides a process by which highly unsaturated fatty acid feedstocks may be converted to free-flowing powder or granular fatty acid calcium salt rumen bypass feed supplements. The use of highly unsaturated fatty acid feedstocks represents a significant departure from conventional processes for the manufacture of fatty acid calcium salt feed supplements.

The process of the present invention may be employed as either a batch or a continuous process. In a typical process according to the present invention, fatty acid feedstocks are added to a production vessel. The mixing should be accomplished in a kettle designed so that intensive and intimate contacting occurs between the calcium oxide and fat admixture so that a homogeneous dispersion of the calcium oxide particles results. Kettles may be either vertical or horizontal in configuration, and there is no need for jacketing for the purpose of heat input since the unit is operated adiabatically (no external heat input or output). The types of internal mixing elements span a wide gap but would include those with propeller, turbine, plows with chopper blades, or preferably 'Cowles-type' mixing blades as examples, but others may apply. These same devices would also be suitable for dispersing and homogenizing the water fraction into the fat admixture and calcium oxide.

Unsaturated fatty acid feedstocks are employed containing from about 50 to about 95% by weight of unsaturated C:16-C:22 fatty acids. The feedstocks should contain no more than about 6% by weight of moisture, insolubles and unsaponifiables and no more than about 20% by weight of the fatty acids should be in the form of glyceride, In general, unsaturated fatty acids having from 16–22 carbon atoms and from I-6 double bonds are suitable for use with the present invention. Polyunsaturated fatty acids are preferred, with conjugated polyunsaturated fatty acids being more preferred, and CLA's being most preferred. Other examples of desirable polyunsaturated fatty acids include Omega-3 and Omega-6 fatty acids.

Essentially, any source of unsaturated fatty acids may be employed, inclusive of fatty acid sources of animal, vegetable or fish origin. This includes distillates and soap stocks of lard, tallow, vegetable oils such as canola oil, sunflower oil, safflower oil, rapeseed oil, soybean oil, olive oil, corn oil, and the like, and byproducts thereof, as well as fish oils and byproducts thereof Pre-treatment processes may be needed to reduce moisture, insolubles, unsaponifiables, and glycerides below about 10% by weight. The level of glycerides, which include monoglycerides, diglycerides and triglycerides, may be reduced by hydrolysis or saponification. Because conjugated polyunsaturated fatty acids are employed, pre-treatment steps may also include isomerization reactions that produce conjugated polyunsaturation.

The unsaturated fatty acid feedstock is preferably selected on the basis of having utility as a human dietary supplement, so that meat and milk from cattle fed the fatty acid calcium salt product therefrom will be enriched therewith with effective amounts thereof CLA's have already been disclosed as having utility as human dietary supplements.

With respect to the particularly preferred CLA's, any isomer having utility as a human dietary supplement may be employed, including the 10,12 and 9,11 isomers and mixtures thereof. Included within the definition of 10,12 isomers are trans 10, trans 12; trans 10, cis 12; cis 10 trans 12 and cis 10 cis 12. The 9,11 isomers likewise include trans 9, trans 11; trans 9, cis 11; cis 9, trans 11 and cis 9, cis 11 isomers. Mixtures of these various 10,12 and 9,11 isomers may also be employed. Likewise, the cis and trans isomers of other mono-and polyunsaturated fatty acids intended for use with the present invention may also be employed, including mixtures thereof.

A particularly preferred CLA feedstock is CLA-60 which is available from Natural, Inc. of Vernon Hills, Ill. CLA-60 contains between about 60 and 70% by weight of various CLA isomers and a total unsaturated fatty acid content of about 90–95 weight percent. Accordingly, to make a commercially acceptable fatty acid calcium salt from CLA-60, greater than 1.75 equivalents of calcium oxide must be employed, or the CLA-60 must be blended with a second fatty acid feedstock having a higher level of saturated fatty acid in an amount effective to provide an admixture containing at least 25% by weight of saturated fatty acids.

In other words, when the amount of calcium oxide employed falls below 1.75 equivalents relative to the amount of fatty acid, the amount of saturated fatty acids in the feedstock must be at a level of 25% by weight or greater. Feedstocks having less than 25% by weight of saturated fatty acids must be blended with a second fatty acid feedstock having greater than 25% by weight of saturated fatty acids in an amount effective to produce at least 25% by weight of saturated fatty acids in the resulting admixture. A preferred source of saturated fatty acids is palm fatty acid distillate (PFAD). The second fatty acid feedstock with higher levels of saturated fatty acids can be present in a blend at a level up to about 5 and about 50% by weight, and preferably between about 5 and about 30% by weight. Such blends can be reacted with greater than 1.75 equivalents of calcium oxide, although such calcium oxide levels are not necessary to produce a commercially acceptable product when saturated fatty acid levels exceed 25% by weight.

Saturated fatty acids have higher melting points than unsaturated fatty acids. Accordingly, it may be necessary to heat the unsaturated fatty acid feedstock to form a uniform, liquid admixture with the second fatty acid feedstock having a combined saturated fatty acid content of 25% by weight or greater. A temperature up to about 80° C. is suitable, with a temperature between about 50 and about 60° C. being preferred.

Calcium oxide is added to the fatty acid feedstock in the range of from about 1.0 to about 2.5 equivalents relative to the fatty acid feedstock. A calcium oxide level above about 1.4 equivalents is preferred, with about 1.75 equivalents being more preferred, so that highly unsaturated fatty acid feedstocks may be employed. A calcium oxide level between about 2.0 and 2.3 equivalents is most preferred. It has been determined that for CLA-60, the optimum fatty acid calcium salt rumen bypass feed supplement is obtained when 2.2 equivalents of calcium oxide is used relative to the CLA-60.

Water is then added to hydrate the calcium oxide to its hydroxide form, creating a large amount of exothermic heat. The heat that is evolved is sufficient for the fatty acid neutralization reaction to proceed to completion, so that it is not necessary to supply heat to the reaction mixture from external sources from this point forward. Between about two and about five equivalents of water relative to the calcium oxide is added to the reaction mixture, with between about 2.5 and about 3.5 equivalents being preferred.

The excess water is converted to steam by the exothermic heat generated, which boils off rapidly. The reaction can be performed under atmospheric pressure, or under vacuum to draw off the steam.

The amount of time required for the reaction is typically between about 5 and about 60 minutes, and more typically between about 6 and about 10 minutes. The reaction is easily identified by the transformation of the admixture into a solid granular mass Upon further agitation, the mass further transforms into a free-flowing granular material, which, upon transfer from the reaction vessel, can easily be processed into free-flowing particles.

A biologically active material can be included as an optional ingredient in the invention process. By the term "biologically active material", it is meant any substance capable of being administered orally in a feed composition. Preferred biologically active materials are susceptible to inactivation in the rumen bimicrobes and digestive juices, and are thereby protected therefrom by incorporation into the fatty acid calcium salts of the present invention. The biologically active material can be selected from a broad variety of nutrients and medicaments, either as a single component or as a mixture of components, which are illustrated by the following list of active molecular species:

1. Sugars and complex carbohydrates which include both water-soluble and water insoluble monosacchandes, disaccharides and polysaccharides. Particularly preferred carbohydrates include cane molasses and sugar beet byproducts.
2. Amino acid ingredients, either singly or in combination, which include arginme, histidine, isoleucine, leucine, lysine, methionine, phenylalanine, threonine, tryptophan, valine, tyrosine ethyl HCl, alanine, aspartic acid, glutamic acid, sodium glutamate, potassium glutamate, glycine, proline, serine, cystine ethyl HCl, and the like; and analogues and salts thereof.
3. Vitamin ingredients, either singly or in combination, including thiamine HCl, riboflavin, pyridoxine HCI, niacin, inositol, choline chloride, calcium pantothenate, biotin, folic acid, ascorbic acid, Vitamin B,Z, p-aminobenzoic acid, Vitamin A acetate, Vitamin K, Vitamin B, Vitamin E, and the like.
4. Trace element ingredients, either singly or in combination, including compounds of cobalt, copper, manganese, iron, zinc, tin, nickel, chromium, molybdenum, iodine, chlorine, silicon, vanadium, selenium, calcium, magnesium, sodium and potassium
5. Protein ingredients obtained from sources such as dried blood or meat meal, meat and bone meal, cottonseed meal, soybean meal, rapeseed meal, sunflower seed meal, canola meal, safflower meal, dehydrated alfalfa, corn gluten meal, soybean protein concentrate, potato protein, dried and sterilized animal and poultry manure, fish meal, fish and poultry protein isolates, crab protein concentrate, hydrolyzed protein feather meal, poultry byproduct meal, liquid or powdered egg, milk whey, egg albumen, casein, fish solubles, cell cream, brewer's residues, and the like.
6. Medicament ingredients, either singly or in combination, including promazine hydrochloride, chloromedoniate acetate, chlorotetracycline, sulfamethazine, monensin, sodium monensin, poloxalme, oxytetracycline, BOVATEC, and the like.
7. Antioxidants, including butylated hydroxyanisole, butylated hydroxytoluene, tertiary butylhydroquinone, tocopherols, propyl gallate and ethoxyquin; and preservatives, including sodium sorbate, potassium sorbate, sodium benzoate, propionic acid, α-hydroxybutenc acid, and the like.

The biologically active material is present at a level up to about 20% by weight relative to the fatty acid.

The unsaturated fatty acid calcium salt rumen bypass feed supplements of the present invention may be conveniently fed to a ruminant admixed with a conventional ruminant feed. The feeds are typically vegetable materials edible by ruminants, such as legume hay, grass hay, corn silage, grass silage, legume silage, corn grain, oats, barley, distiller's grain, brewer's grain, soya bean meal and cottonseed meal. According to U.S. Pat. No. 5,143,737 ruminants were fed between 2 and 15% by weight, and preferably between about 3 and 10% by weight of rumen-protected unsaturated fatty acids to produce the modified milk fat and meat fat. There is no particular lower limit of the calcium salt to be added to the ruminant feed, although in practice, amounts of the calcium salt below about 1% of the dry solids content of the feed are too small to provide significant modification of the milk or meat fat.

Ruminants fed the unsaturated fatty acid calcium salts of the present invention produce a higher level of unsaturated milk fat and meat fat. The food products having more unsaturated fat and less saturated fat are useful as food products for mammals, especially human beings. The following non-limiting examples set forth herein below illustrate certain aspects of the invention All parts and percentages are by weight unless otherwise noted, and all temperatures are in degrees Celsius.

EXAMPLES

Example 1

13.8 pounds of calcium oxide was added to a vertical mixer with Cowles-type mixing blades containing 69.6 pounds CLA-60. The CLA-60 had by concentration 65% by weight CLA and 95% by weight free fatty acid. The total unsaturated fatty acid content was 90% by weight. Prior to adding the calcium oxide, the CLA-60 was heated to a temperature of 60° C. After the calcium oxide was uniformly dispersed, 10.8 pounds of water was added, and the temperature of the mixture rose to 120° C. Agitation continued until a uniform, homogenous mixture was obtained, which was dumped from the vessel into a tray, in which the reaction went to completion and the product cooled. Milling of the finished product produced a free-flowing granule that was not dusty having a total fat content of about 83% by weight.

Example 2

33.8 pounds of palm fatty acid distillate (PFAD) was added to 68.5 pounds of CLA-60 heated to a temperature 60° C. and agitated until a uniform, homogenous mixture was obtained. 18.4 pounds of calcium oxide was added with further agitation. After the calcium oxide was uniformly dispersed, 15.2 pounds of water was added, and the temperature of the mixture rose to 120° C. The product was recovered as an Example 1 and had an 85% by weight fat content.

A free-flowing granular product was obtained despite the reduced amount of calcium oxide relative to the fat content The calcium oxide content was equivalent to 20% by weight relative to CLA plus 14% by weight relative to PFAD).

Example 3

The following ingredients were reacted according to the process of Example 2
4,884 lbs. CLA
2,085 lbs. PFAD
1,504 lbs. Calcium Oxide
1,716 lbs. Water A free-flowing granular product was obtained having a total fat content of 82.25% by weight.

Examples 5–9

The following examples demonstrate the importance of using higher levels of calcium oxide or higher levels of saturated fatty acids. Oleic acid calcium salt were prepared according to the method of Example I for Examples 5–8, and according to the method of Example 2 for Example 9. The quantities employed are depicted in Table 1:

TABLE I

|  | #5 | #6 | #7 | #8 | #9 |
|---|---|---|---|---|---|
| PFAD | — | — | — | — | 9 |
| Oleic | 300 | 300 | 300 | 300 | 210 |
| C$_a$O | 45 | 75 | 45 | 60 | 60 |
| H$_2$O | 50 | 80 | 50 | 65 | 65 |
| Temp F. | 80 | 140 | 135 | 135 | 140 |

Examples 5 and 7 resulted in a tough material that could not be properly granulated, although Example 7 showed some improvement. Example 6 was the best product from a commercial perspective. Example 8 was an improvement over Examples 5 and 7, but Example 9 was even better and was also commercially acceptable.

The present invention thus provides a method by which rumen-protected fatty acid calcium salts may be prepared in a form familiar to and accepted by the dairy and cattle industry for supplementation of cattle diets to produce meat and milk products enriched in unsaturated fatty acids that are of interest in human nutrition. The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A method for the preparation of free-flowing calcium salts of highly unsaturated fatty acids comprising:
   (a) providing an unsaturated fatty acid feedstock consisting essentially of:
      (i) from about 50 to about 95% by weight of unsaturated C:16-C:22 fatty acids;
      (ii) from about 5 to about 40% by weight of saturated C:14-C:22 fatty acids; and
      (iii) no more than about 6% by weight of moisture, insolubles and unsaponifiables,
      with no more than about 20% by weight of said unsaturated feedstock being in the form of glycerides;
   (b) adding to said unsaturated feedstock from about 1.0 to about 2.5 equivalents of calcium oxide relative to the unsaturated feedstock, so that a reactive admixture is formed; and
   (c) adding to said reactive admixture from about 2 to about 5 equivalents of water relative to said calcium oxide, so that said calcium oxide hydrates and neutralizes said fatty acids to form said calcium salts;
   provided that when less than 1.75 equivalents of calcium oxide is added, said unsaturated feedstock comprises at least 25% by weight of said saturated fatty acids and is heated to a temperature above its melting point before said step of adding said calcium oxide.

2. The method of claim 1, wherein said unsaturated feedstock comprises polyunsaturated fatty acids.

3. The method of claim 1, wherein said unsaturated feedstock comprises oleic acid.

4. The method of claim 3, wherein unsaturated feedstock comprises greater than about 90% by weight of oleic acid.

5. The method of claim 1, wherein less than 1.75 equivalents of said calcium oxide is employed relative to the total amount of said unsaturated feedstock.

6. The method of claim 1, wherein said unsaturated feedstock comprises from about 5 to about 30% by weight of PFAD.

7. The method of claim 6, wherein less than 1.75 equivalents of said calcium oxide is employed relative to said unsaturated feedstock.

8. The method of claim 1, further comprising the step of cooling said admixture and forming a solid, free-flowing and granular fatty acid calcium salt product.

9. The method of claim 1, further comprising the step of adding a biologically active material to said admixture.

10. The method of claim 9, wherein said biologically active material is an amino acid.

11. A free-flowing highly unsaturated fatty acid calcium salt that is stable against oxidation, prepared by the method of claim 1.

12. A free-flowing unsaturated fatty acid calcium salt product comprising from about 0.1 to about 1.5 equivalents of calcium hydroxide relative to the fatty acid content of said product, said fatty acid content consisting essentially of (a) from about 50 to about 95% percent by weight of unsaturated C:16-C:22 fatty acids;
   (b) from about 5 to about 40% by weight of saturated C:14-C:22 fatty acids;
   (c) no more than about 6% by weight of moisture, insolubles and unsaponifiables, and
   with no more than about 20% by weight being in for form of glycerides;

provided that when less than 0.75 equivalents of said calcium hydroxide calcium oxide is present, said fatty acid content comprises at least 25% by weight of said saturated fatty acids.

13. The fatty acid calcium salt product of claim 12, wherein said unsaturated C:16-C:22 fatty acids comprise one or more fatty acids selected from the group consisting of Omega-3 and Omega-6 fatty acids.

* * * * *